United States Patent [19]
Buendgen

[11] Patent Number: 5,866,763
[45] Date of Patent: Feb. 2, 1999

[54] INBRED CORN LINE ZS01220

[75] Inventor: Michael B. Buendgen, Madison, Wis.

[73] Assignee: Zenco (No. 4) Limited, London, England

[21] Appl. No.: 719,841

[22] Filed: Sep. 30, 1996

[51] Int. Cl.⁶ .............................. A01H 5/00; A01H 4/00; A01H 14/00; C12N 5/04

[52] U.S. Cl. ...................... 800/200; 800/235; 800/250; 800/DIG. 56; 435/412; 435/424; 435/430; 435/430.1; 47/58; 47/DIG. 1

[58] Field of Search ..................................... 800/200, 205, 800/235, 250, DIG. 56; 435/412, 424, 430, 430.1; 47/58, DIG. 1

[56] References Cited

PUBLICATIONS

Coe, E.H., Jr. and M.G. Neuffer. The Genetics of Corn, p. 111.
Conger, B.V., F.J. Novak, R. Afza, and K. Erdelsky. "Somatic embryogenesis from cultured leaf segments of *Zea mays*", Plant Cell Reports, 6:345–347 (1987).
Duncan, D.R., M.E. Williams, B.E. Zehr and J.M. Widholm. "The production of callus capable of plant regenerationf rom immature embryos of numerous *Zea mays* genotypes", Planta, 165:322–332 (1985).
Edallo, et al., "Chromosomal Variation and Frequency of Spontaneous Mutation Associated with in Vitro Culture and Plant Regeneration in Maize" Maydica XXVI, pp. 39–56 (1981).
Forsberg, R.A. and R.R. Smith. "Sources, Maintenance, and Utilization of Parental Material", Hybridization of Crop Plants, Chapter 4, pp. 65–81 (1980).
Green, C.E. and R.L. Phillips. "Plant Regeration from Tissue Cultures of Maize", Crop Science, vol. 15, pp. 417–421 (1975).
Green, C.E. and C.A. Rhodes. "Plant Regeneration in Tissue Cultures of Maize", Maize for Biological Research, pp. 367–372 (1982).
Hallauer, et al, "Corn Breeding", Corn and Corn Improvement pp. 463–564 (1988). Sprague et al, eds.
Lowe, Keith. Patent Application 0 160 390.
Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Crop Science, vol. 24, pp. 545–549 (1984).
Phillips, et al., "Cell/Tissue Culture and In Vitro Manipulation", In Corn & Corn Improvement, 3rd Ed., ASA Publication, #18, pp. 345–349 & 356–357 (1988).
Poehlman, John Milton. *Breeding Field Crop*, AVI Publishing Company, Inc., Westport, Connecticut, pp. 237–246 (1987).
Rao, K.V., et al., "Somatic Embryogenesis in Glume Callus Cultures", Osmania University, Hyberabad, India.
Sass (1977) "Morphology". In Corn & Corn Improvement. ASA Publication. Madison, WI, pp. 89–109.
Songstad, David D., David R. Duncan, and Jack M. Widholm. "Effect of 1–aminocyclopropane–1–carboxylic acid, silver nitrate, and norbornadiene on plant regeneration from maize callus cultures", Plant Cell Reports, 7:262–265 (1988).
Tomes, et al, "the Effect of Parental Genotype on Initiation of Embryogenic Callus from Elite maize (*Zea mays* I.) Germplasm". Theor. Appl. Genet. 70., pp. 505–509. (1985).
Troyer, et al., "Selection for Early Flowering in Corn: 10 Late Synthetics". Crop Science, vol. 25, pp. 695–697 (1985).
Umbeck, et al. "Reversion of Male–Sterile T–Cytoplasm Maize to Male Fertility in Tissue Culture", Crop Science vol. 23, pp. 584–588 (1983).
Wright, H., "Commercial Hybrid Seed Production", Hybridization of Crop Plants, pp. 161–176, (1980).
Wych, R.D., "Production of Hybrid Seed Corn"; Corn and Corn Improvement, pp. 565–607 (1988).
Evans et al. Somaclonal and gametoclonal variation. American Journal of Botany. 71(6):759–774, 1984.
Evans, D.A. Somaclonal variation—genetic basis and breeding applications. 5(2):46–50, 1989.
Potrykus, I. Gene transfer to cereals: an assessment. Bio/Technology. 8(6):535–542, Jun. 1990.
Finnegan et al. Transgene inactivation: plants fight back! Bio/Technology. 12:883–888, Dec. 1994.

*Primary Examiner*—Gary Benzion
*Assistant Examiner*—Thanda Wai
*Attorney, Agent, or Firm*—Dana Rewoldt

[57] ABSTRACT

Broadly this invention provides inbred corn line ZS01220. The methods for producing a corn plant by crossing the inbred line ZS01220 are encompassed by the invention. Additionally, the invention relates to the various parts of inbred ZS01220 including culturable cells. This invention relates to hybrid corn seeds and plants produced by crossing the inbred line ZS01220 with at least one other corn line.

22 Claims, No Drawings

INBRED CORN LINE ZS01220

FIELD OF THE INVENTION

This invention is in the field of corn breeding, specifically relating to an inbred corn line designated ZS01220.

BACKGROUND OF THE INVENTION

The original maize plant was indigenous to the Western Hemisphere. The plants were weedlike and only through the efforts of early breeders was a cultivated crop species developed. The crop cultivated by early breeders like the crop today could be wind pollinated. The physical traits of maize are such that self pollination or cross pollination between plants can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. A large part of the development of the maize product in to a profitable agricultural crop was due to the work done by land grant colleges. Originally, maize was an open pollinated variety having heterogeneous genotypes. The maize farmer selected uniform ears from the yield of these genotypes and reserved them for planting the next season. The result was a field of maize plants that were segregating for a variety of traits. This type of maize selection lead to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with other inbred lines to produce hybrid progeny (F1). Although hybrids are robust and vigorous plants due to heterosis, inbred lines are less vigorous and can be difficult to produce since the inbreeding process in corn decreases the vigor. However, when two inbred lines are crossed, the hybrid plant evidences greatly increased vigor compared to open pollinated segregating maize plants. An important factor of the homozygosity and the homogeneity of the inbred lines is that the hybrid from any cross will always be the same, and can be reproduced.

The ultimate objective of the commercial maize seed companies is to produce high yielding, ergonomically sound plants which perform well in certain regions or areas of the Corn Belt. To produce these types of hybrids, the companies must develop inbreds which carry needed traits into the hybrid combination. Hybrids are not uniformly adapted for the Corn Belt, but are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois soil. Thus, a variety of major agronomic traits are important in hybrid combination for the various Corn Belt regions, and have an impact on hybrid performance.

Inbred line development and hybrid testing have been emphasized in the past half century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low level of organic matter, clay, sand, black, high pH, low pH; performance in: wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and agronomics of inbreds and resultant commercial hybrids.

SUMMARY OF THE INVENTION

The present invention relates to an inbred corn line ZS01220. Specifically, this invention relates to plants and seeds of this line. Additionally, this relates to a method of producing hybrid seed corn from this inbred. More particularly, this invention relates to the unique combination of traits that combine in corn line ZS01220.

Generally then, broadly the present invention includes an inbred corn seed designated ZS01220. This seed produces a corn plant.

The invention also includes the tissue culture of regenerable cells of ZS01220 wherein the tissue regenerates plants having the genotype of ZS01220. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS01220 having ZS01220's genotype.

The invention extends to hybrid seed produced by planting, in pollinating proximity, seeds of corn inbred lines ZS01220 and another inbred line; cultivating corn plants resulting from said planting; preventing pollen production by the plants of one of the inbred lines; allowing natural cross pollinating to occur between said inbred lines; and harvesting seeds produced on plants of the inbred. The hybrid seed produced by hybrid combination of plants of inbred corn seed designated ZS01220 and plants of another inbred line. Hybrid plants grown from this hybrid seed.

The invention further includes a method of hybrid F1 production. A first generation (F1) hybrid corn plant produced by the process of planting, seeds of corn inbred line ZS01220; cultivating corn plants resulting from said planting; permitting pollen from another inbred line to cross pollinate inbred line ZS01220; harvesting seeds produced on plants of the inbred; and growing a harvested seed.

A first generation (F1) hybrid corn plant produced by the process of planting, seeds of corn inbred line ZS01220; cultivating corn plants resulting from said planting; permitting pollen from inbred line ZS01220 to cross pollinate another inbred line; harvesting seeds produced on plants of the inbred; and growing a harvested seed.

The inbred corn line ZS01220 and at least one transgenic gene adapted to give ZS01220 additional insect resistance or herbicide resistance or disease resistance.

The inbred corn line ZS01220 and at least one transgenic gene adapted to give ZS01220 modified starch traits. The inbred corn line ZS01220 and at least one mutant gene adapted to give ZS01220 modified starch or oil traits. The inbred corn line ZS01220 and at least one transgenic gene selected from the group consisting of: bacillus thuringiensis, the bar or pat gene encoding Phosphinothricin acetyl Transferase, EPSP synthase gene, low phytic acid producing gene, zein. The inbred corn line ZS01220 and at least one transgenic gene useful as a selectable marker or a screenable marker.

A tissue culture of the regenerable cells of hybrid plants produced with use of ZS01220 genetic material. A tissue culture of the regenerable cells of the corn plant produced by the method described above.

DEFINITIONS

In the description and examples which follow, a number of terms are used. In order to provide a clear and consistent understanding of the specifications and claims, including the scope to be given such terms, the following definitions are provided.

BL Moist

The moisture percentage of the grain at black layer, i.e., when 50% of the plants per plot have reached physiological maturity.

Cold Germ

Cold Germ is a measurement of seed germination under cold soil conditions. Data is reported as percent of seed germinating.

ECB

European corn borer a maize eating insect. ECBI is the first brood generation of European corn borers. ECBII is the second generation of European corn borers.

Emerge

The number of emerged plants per plot (planted at the same seedling rate) collected when plants have two fully developed leaves.

GI

This is a selection index which provides a single quantitative measure of the worth of a hybrid based on four traits. Yield is the primary trait contributing to index values. The GI value is calculated by combining stalk lodging, root lodging, yield and dropped ears according to the attached mathematical formula:

$$GI=100+0.5(YLD)-0.9(\% \ STALK \ LODGE)-0.9(\% \ ROOT \ LODGE)-2.7(\% \ DROPPED \ EAR)$$

GLS

Gray Leaf Spot (*Cercospora zeae*) disease rating. This is rated on a 1–9 scale with a "1" being very susceptible, and a "9" being very resistant.*

GW

Goss' Wilt (*Corynebacterium nebraskense*). This is rated on a 1–9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp}(°F.) + \text{Min } Temp(°F))}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

$MDMV_B$

Maize Dwarf Mosaic Virus strain B. This is rated on a 1–9 scale with a "1" being very susceptible and a "9" being very resistant.*

Moisture

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

PCT Tiller

The total number of tillers per plot divided by the total number of plants per plot.

Plant

This term includes plant cells, including haploid cells, transgenic cells integrated into the plant genome, plant protoplasts, plant cell tissue cultures from which corn plants can be regenerated, plant calli, plant clumps, meristematic tissue, and plant cells that are intact in plants or parts of plants, such as embryos, pollen, ovules, flowers, kernels, ears, cobs, leaves, husks, stalks, roots, root tips, anthers, silks and the like.

Plant Height

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

Shed

The volume of pollen shed by the male flower rated on a 1–9 scale where a "1" is a very light pollen shedder, a "4.5" is a moderate shedder, and a "9" is a very heavy shedder.

SLB

Southern Leaf Blight (*Bipolaris maydis*) disease rating. This is rated on a 1–9 scale with a "1" being very susceptible, and a "9" being very resistant.*

TWT

The measure of the weight of grain in pounds for a one bushel volume adjusted for percent grain moisture.

Vigor

Visual rating of 1 to 9 made 2–3 weeks post-emergence where a "1" indicates very poor early plant development, and a "9" indicates superior plant development.

Warm Germ

A measurement of seed germination under ideal (warm, moist) conditions. Data is reported as percent of seeds germinating.

Yield (YLD)

Actual yield of grain at harvest adjusted to 15.5% moisture. Measurements are reported in bushels per acre.

% Dropped Ears (DE)

The number of plants per plot which dropped their primary ear divided by the total number of plants per plot.

% LRG Flat

Percentage by weight of shelled corn that passes through a $26/64$ inch round screen and a $14/64$ inch slot screen, but does not pass through a screen with $20.5/64$ inch round openings.

% LRG Round

Percentage by weight of shelled corn that passes through a $26/64$ inch round screen, but does not pass through a $14/64$ inch slot screen or a screen with $20.5/64$ inch round openings.

% MED Flat

Percentage by weight of shelled corn that passes through a $20.5/64$ inch round screen and a $13/64$ inch slotted screen, but does not pass through a screen with $17/64$ inch round openings.

% MED Round

Percentage by weight of shelled corn that passes through a $20.5/64$ inch round screen, but does not pass through a $13/64$ inch slot screen or a screen with $17/64$ inch round openings.

% SML Flat

Percentage by weight of shelled corn that passes through a $17/64$ inch round screen and a $12/64$ inch slotted screen, but does not pass through a screen with $15/64$ inch round openings.

% SML Round

Percentage by weight of shelled corn that passes through a 17/64 inch round screen, but does not pass through a 12/64 inch slotted screen or a screen with 15/64 inch round openings.

% Root Lodge (RL)

Percentage of plants per plot leaning more that 30 degrees from vertical divided by total plants per plot.

% Stalk Lodge (SL)

Percentage of plants per plot with the stalk broken below the primary ear node divided by the total plants per plot.

*Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

ZS01220 can be used as a female or male line due to its pollen shed (about 6) and seed production abilities. This ZS01220 line shows good general combining ability and specific combining ability with inbreds, especially iodents such as produced by Iowa State University.

This inbred shows good seed grade out (very low percentage are small rounds or small flats) and good germination quality and high inbred seed yield. This inbred has unique light green colored leaves. This line makes big robust hybrids that carry outstanding cold germination which is an essential trait for inbreds that are adapted to the upper northern cornbelt region. Also this line possesses good tolerance to a number of diseases such as Northern Corn Leaf Blight, Eyespot, and Gray Leaf Spot.

The inbred has shown uniformity and stability within the limits of environmental influence for all the traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS01220.

The best method of producing the invention, ZS01220 which is substantially homozygous, is by planting the seed of ZS01220 which is substantially homozygous and self-pollinating or sib pollinating the resultant plant in an isolated environment, and harvesting the resultant seed or the resultant pollen. Likewise the best method of producing a ZS01220 hybrid is to plant the hybrid seed. Alternatively a method of producing a ZS01220 hybrid includes planting the inbred seed of ZS01220 (using it as either a male of a female) and crossing it with a second inbred and harvesting the hybrid seed therefrom.

TABLE 1

ZS01220
VARIETY DESCRIPTION INFORMATION

1 Type: Dent
2 Region Best Adapted: Broadly adapted - south and central Wisconsin; south and central Minnesota; Michigan; Ontario, Canada; and northern Iowa.
ZS01220's maturity as a line makes hybrids adapted to these regions.

CORN PLANT MORPHOLOGICAL DESCRIPTION
INBRED ZS01220

| PLANT TRAITS | | LEAF TRAITS | |
|---|---|---|---|
| PLANT HEIGHT | 74 IN. | LEAVES ABOVE EAR | 6 |
| EAR HEIGHT | 40 IN. | LEAVES BELOW EAR | 6 |
| BRACE ROOT COLOR | YELLOW/ GREEN | LEAF ANGLE ABOVE EAR | SEMI-ERECT |
| SHOOTS AT FLOWERING | LEAFY | LEAF ANGLE BELOW EAR | SEMI-ERECT |
| SILK COLOR | PALE GREEN | FLAG LEAF ANGLE | SEMI-ERECT |
| COB COLOR | RED | LEAF COLOR | MEDIUM GREEN |
| KERNEL ROWS | 14 | LEAF MARGIN COLOR | RED |

TABLE 1-continued

| TASSEL TRAITS | | EAR AND KERNEL TRAITS | |
|---|---|---|---|
| TASSEL SIZE | 15 IN. | EAR LENGTH | 5 IN. |
| NUMBER OF BRANCHES | 3 | EAR DIAMETER | 1.5 IN. |
| TASSEL BRANCH ANGLE | ERECT | COB DIAMETER | IN. |
| GLUME COLOR | GREEN | KERNEL CROWN COLOR | LIGHT YELLOW |
| ANTHER COLOR | PURPLISH-BROWN | KERNEL BODY COLOR | DARK YELLOW |
| GLUME RING COLOR | WHITE | | |

ZS01220

| #4 DISEASE RESISTANCE | Northern leaf blight = 7.0 |
| --- | --- |
| | NLSr2* = — |
| | Gray leaf spot = 6.0 |
| | Eye = visually good resistance |
| | GW = — |
| | MDMVB = 3.0 |

5 The comparable inbreds to ZS01220 are ZS0114 having the designation of PVP 9400260, and a parent line ZS0448.

*Northern Leaf Spot Race Two

The Munsell code is a reference book of color which is known and used in the industry and by persons with ordinary skill in the art of plant breeding.

The purity and homozygosity of inbred ZS01220 is constantly being tracked using isozyme genotypes as shown in Table 2.

Isozyme Genotypes for ZS01220

Isozyme data were generated for inbred corn line ZS01220 according to procedures known and published in the art. The data in Table 2 gives the electrophoresis data on ZS01220.

TABLE 2

ELECTROPHORESIS RESULTS FOR ZS01220

| INBRED | ACP1 | ACP4 | ADH | MDH1 | MDH2 | PGD1 | PGD2 | PH1 | PGM | IDH2 |
|---|---|---|---|---|---|---|---|---|---|---|
| ZS01220 | 33 | 33 | 22 | 22 | 22 | 11 | 11 | 22 | 22 | 11 |

Inbred and Hybrid Performance of ZS01220

The traits and characteristics of inbred corn line ZS01220 are listed to compare with other inbreds and/or in hybrid combination. ZS01220 data shows the characteristics and traits of importance, giving a snapshot of ZS01220 in these specific environments.

Table 3A shows a comparison between ZS01220 and a comparable inbred ZS0448. Both inbreds are adapted to the northern region of the corn Belt, although the parent is slightly earlier in both pollination dates and in silking dates. The vigor of the two inbreds is similar as is the emergence data. However there is clearly a significant difference in the male capabilities between the two inbreds. The parent is not useful as a male with a pollen shed of 3.5. However the present invention clearly is capable of being used as a male due to the shed rating of approximately 6. Additionally, the yield indicates that the present invention is also an improvement of its parent in seed yield. The female capabilities of the present invention are superior to the inbred ZS0448. The present invention also carries better warm germination characteristics and cold germination characteristics then does ZS0448. These characteristics are critical in placing a hybrid combination in the Northern region of the Corn belt.

TABLE 3A

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS01220 | 6.3 | 82.8 | | 166.8 | 82.5 | 5.8 | | |
| | ZS0448 | 6.5 | 83.8 | | 170.9 | 77.9 | 3.5 | | |
| | # EXPTS | 4 | 4 | | 4 | 4 | 4 | | |
| | DIFF | 0.3 | 1.0 | | 4.1 | 4.6 | 2.3 | | |
| | PROB | 0.638 | 0.667 | | 0.665 | 0.574 | 0.098*** | | |

| YEAR | INBRED | HEATP10 | HEATP50 | HEATP90 | HEATS10 | HEATS50 | HEATS90 |
|---|---|---|---|---|---|---|---|
| OVERALL | ZS01220 | 1400 | 1452 | 1572 | 1439 | 1483 | 1521 |
| | ZS0448 | 1268 | 1333 | 1462 | 1339 | 1379 | 1420 |
| | # EXPTS | 4 | 4 | 4 | 4 | 4 | 4 |
| | DIFF | 132 | 119 | 110 | 100 | 104 | 101 |
| | PROB | 0.002* | 0.010* | 0.004* | 0.005* | 0.020** | 0.021** |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS0 220 | 1333 | 2559 | | | | | 11.5 | 86.3 |
| | ZS0448 | 1181 | 2470 | | | | | 11.5 | 66.8 |
| | # EXPTS | 4 | 1 | | | | | 4 | 4 |
| | DIFF | 152 | 89 | | | | | 0.0 | 19.5 |
| | PROB | 0.004* | | | | | | 0.974 | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS01220 | 94.4 | 89.4 | 16.3 | 18.3 | 36.3 | 25.7 | 2.3 | 1.0 |
| | ZS0448 | 90.3 | 84.9 | 4.7 | 8.0 | 26.0 | 44.7 | 8.0 | 6.3 |
| | # EXPTS | 4 | 4 | 3 | 3 | 3 | 3 | 3 | 3 |
| | DIFF | 4.1 | 4.5 | 11.7 | 10.3 | 10.3 | 19.0 | 5.7 | 5.3 |
| | PROB | 0.008* | 0.223 | 0.108 | 0.042** | 0.216 | | | |

Table 3B compares ZS01220 with ZS0114 which corresponds to the PVP given above. ZS01220 evidences better yield by approximately 39 bushels and has slightly higher grain moisture at harvest than does ZS0114. This line is almost as good as a male as ZS0114 but is better as a female then ZS0114 due to its enhanced inbred seed yield capabilities. ZS01220 has slightly more seedling vigor and shows significant difference in Heat units to 90% pollen and 10% silks and 50% silks.

TABLE 3B

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS01220 | 6.3 | 82.8 | | 166.8 | 82.5 | 5.8 | | |
| | ZS0114 | 6.0 | 78.5 | | 164.6 | 85.4 | 6.5 | | |
| | # EXPTS | 4 | 4 | | 4 | 4 | 4 | | |

TABLE 3B-continued

PAIRED INBRED COMPARISON DATA

|  |  |  |  |  |  |  |  |
|---|---|---|---|---|---|---|---|
| DIFF | 0.2 | 4.3 |  | 2.2 | 2.9 | 0.8 |  |
| PROB | 0.495 | 0.374 |  | 0.871 | 0.881 | 0.058*** |  |

| YEAR | INBRED | HEATP10 | HEATP50 | HEATP90 | HEATS10 | HEATS50 | HEATS90 |
|---|---|---|---|---|---|---|---|
| OVERALL | ZS01220 | 1400 | 1452 | 1572 | 1439 | 1483 | 1521 |
|  | ZS0114 | 1422 | 1463 | 1643 | 1481 | 1518 | 1553 |
|  | # EXPTS | 4 | 4 | 4 | 4 | 4 | 4 |
|  | DIFF | 22 | 12 | 71 | 42 | 35 | 32 |
|  | PROB | 0.282 | 0.656 | 0.028** | 0.005* | 0.013** | 0.201 |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS01220 | 1333 | 2559 |  |  |  |  | 11.5 | 86.3 |
|  | ZS0114 | 1305 | 2585 |  |  |  |  | 11.4 | 47.1 |
|  | # EXPTS | 4 | 1 |  |  |  |  | 4 | 4 |
|  | DIFF | 27 | 26 |  |  |  |  | 0.1 | 39.1 |
|  | PROB | 0.433 |  |  |  |  |  | 0.942 |  |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS01220 | 94.4 | 89.4 | 16.3 | 18.3 | 36.3 | 25.7 | 2.3 | 1.0 |
|  | ZS0114 | 94.3 | 84.4 | 4.3 | 15.0 | 39.7 | 34.3 | 4.3 | 1.7 |
|  | # EXPTS | 4 | 4 | 3 | 3 | 3 | 3 | 3 | 3 |
|  | DIFF | 0.1 | 5.0 | 12.0 | 3.3 | 3.3 | 8.7 | 2.0 | 0.7 |
|  | PROB | 0.950 | 0.392 | 0.059*** | 0.063*** | 0.428 |  |  |  |

Table 4 shows the GCA (general combining ability) estimates of ZS01220 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and ICI Seeds' commercial products and pre-commercial hybrids which were grown in the same sets and locations.

TABLE 4A

| | N | FI | Y/M | GI | YLD | MST | % SL | % RL | % DE | TWT | POP | RM |
|---|---|---|---|---|---|---|---|---|---|---|---|---|
| | | | | | ZS01220 | | | | | | | |
| XR = | 114 | 1.4 | 0.1 | 1.5 | 2.7 | 0.0 | −0.4 | 0.5 | 0.0 | 0.6 | −29 | 121 |

Table 4A shows ZS01220 in XR crossed to 11 different inbreds to form 114 hybrid combinations. ZS01220 in hybrid combination shows an excellent advantage for yield (YLD) and a good advantage for yield by moisture (Y M) compared to the commercial checks and the company's commercial inbreds. ZS01220 has a good rating for most of the agronomic traits of resistance to root lodging and dropped ears.

TABLE 4B

| | N | FI | Y/M | GI | YLD | MST | % SL | % RL | % DE | TWT | POP | RM |
|---|---|---|---|---|---|---|---|---|---|---|---|---|
| | | | | | ZS01220 | | | | | | | |
| XR = | 114 | 1.4 | 0.1 | 1.5 | 2.7 | 0.0 | −0.4 | 0.5 | 0.0 | 0.6 | −29 | 121 |

TABLE 4B-continued

|  | N | FI | Y/M | GI | YLD | MST | % SL | % RL | % DE | TWT | POP | RM |
|---|---|---|---|---|---|---|---|---|---|---|---|---|
|  |  |  |  |  |  | ZS0114 |  |  |  |  |  |  |
| XR = | 2298 | 2.1 | 0.3 | −0.3 | −0.8 | 1.1 | 0.1 | −0.3 | 0.1 | 0.0 | −44 | 102 |
|  |  |  |  |  |  | ZS0448 |  |  |  |  |  |  |
| XR = | 1134 | −0.3 | 0.2 | −2.7 | −5.2 | 1.1 | −0.2 | 0.1 | 0.0 | −0.3 | −107 | 95 |

Table 4B compares ZS01220 in random hybrid combinations with ZS0114, and ZS0448 in random combinations. ZS01220 has an advantage in many categories over ZS0114. ZS01220 has less of an advantage in stalk lodging and moisture than either of the other two. However, ZS01220 has an advantage in test weight, yield and root lodging over ZS0114, and ZS0448 in each of the other categories. As is evidenced by the GI index, the inbred ZS01220 has the best, most consistent inbred package to bring into the hybrid combination.

TABLE 5

YIELD RESPONSE

| HYBRID | YIELD | | | | | |
|---|---|---|---|---|---|---|
| ZS01220/Inbred | 90.1 | 112.6 | 135.1 | 157.6 | 180.1 | 202.6 |
| Environment | 75 | 100 | 125 | 150 | 175 | 200 |

Table 5 shows the yield response of ZS01220 in hybrid combination in comparison with the plants in the environment around it at the same location. ZS01220 in hybrid combination yields well in low, medium and high yielding environments. Its best performance is in low/moderate yielding environments.

TABLE 6A

HYBRID SUMMARY
ZS01220/INBRED
PERFORMANCE DATA

| HYBRID | N | FI | GI | YLD | MST |
|---|---|---|---|---|---|
| ZS01220/CT | 25 | 127 (8) | 172 (5) | 153 (7.9*) | 19.5 (1.4*) |
| 8746 | 25 | 119 | 167 | 145.0 | 20.8 |

*significant difference at the 0.1 level
CT = common tester
(#) = difference between two hybrids Table 6A shows in positive numbers the advantage the ZS01220 hybrid has over a commercially available ICI Seeds' hybrid. ZS01220 hybrid compares favorably with this hybrid. the ZS01220 hybrid is better yielding and has lower moisture across years. Although not shown above the roots and stalks and dropped ears of the two hybrids is substantially equivalent, the two hybrid combinations are adapted to the same zone of the Corn Belt; however, ZS01220 in hybrid comparison has significantly better yield and moisture results than 8746.

TABLE 6B

HYBRID SUMMARY
ZS01220/INBRED
AGRONOMIC DATA

| HYBRID | N | EMERGE | VIGOR | PLANT HEIGHT | EAR HEIGHT | PLANT INTEGRITY |
|---|---|---|---|---|---|---|
| ZS01220 | 22 | 5.79 | 6.6 | 94.7 | 46.2 | 6.7 |
| 8746 | 22 | 4.8 | 5.4 | 94.5 | 46.5 | 6.8 |

Table 6B shows the advantages and disadvantages generated by comparison of the agronomic data of 8746 with the ZS01220 hybrid. ZS01220 has a better emerged rating in this years environment then does 8746. Additionally, ZS01220 shows seedling vigor of 6.6 an advantage over 8746.

The inbred ZS01220 can be employed as the female or the male plant in a hybrid production field. This inbred is adapted to a wide geographical area. This makes it highly compatible with a number of different inbred for crossing. The plant shows excellent late season plant integrity and good disease resistance. This inbred carries not only its yield ability into the hybrid but it also carries good agronomic traits such as good plant integrity and root quality. Additionally this maize can within the scope of the invention contain: a mutant gene such as but not limited to sugary 1 or shrunken 1 or waxy or AE or imazethapyr tolerant (IT or $IR_{TM}$) mutant gene; or transgenic genes such as but not limited to insect resistant genes such as Bacillus thuringiensis (Cry genes), or herbicide resistant genes such as Pat gene or Bar gene ESPS, or disease resistant genes such as the Mosaic virus resistant gene, etc.

In hybrid combination, ZS01220 carries good yield for moisture characteristics into the hybrid. This inbred has strong general combining and specific combining ability for yield, with most lines, especially iodents. ZS01220 is a versatile line. This ZS01220 inbred makes early hybrids.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line ZS01220. Further, both first and second parent corn plants can come from the inbred corn line ZS01220. A variety of breeding methods can be selected depending on the mode of reproduction, the trait, the condition of the germplasm. Thus, any such methods using the inbred corn line ZS01220 are part of this invention: selfing, backcrosses, hybrid production, crosses to populations, haploid and anther culturing and the like.

Various culturing techniques known to those skilled in the art, such as haploid, (stock six is a method that has been in use for twenty years and is well known to those with skill in the art), transformation, and a host of other conventional and unconventional methods are within the scope of the invention. All plants and plant cells produced using inbred corn line ZS01220 are within the scope of this invention. The term transgenic plant refers to plants having exogenous genetic sequences which are introduced into the genome of a plant by a transformation method and the progeny thereof.

Transformation Methods—are means for integrating new genetic coding sequences by the incorporation of these sequences into a plant of new genetic sequences through man assistance.

Though there are a large number of known methods to transform plants, certain types of plants are more amenable to transformation than are others. Tobacco is a readily transformable plant. The basic steps of transforming plants are known in the art. These steps are concisely outlined in U.S. Pat. No. 5,484,956 "Fertile Transgenic *Zea mays* Plants Comprising Heterologous DNA Encoding *Bacillus thuringiensis* Endotoxin" issued Jan. 16, 1996 and U.S. Pat. No. 5,489,520 "Process of Producing Fertile *Zea mays* Plants and Progeny Comprising a Gene Encoding Phosphinothricin Acetyl Transferase" issued Feb. 6, 1996.

1. Plant Lines

Plant cells such as maize can be transformed by a number of different techniques. Some of these techniques which have been reported on and are known in the art include maize pollen transformation (See University of Toledo 1993 U.S. Pat. No. 5,177,010); Biolistic gun technology (See U.S. Pat. No. 5,484,956); Whiskers technology (See U.S. Pat. Nos. 5,464,765 and 5,302,523); Electroporation; PEG on Maize; Agrobacterium (See 1996 article on transformation of maize cells in *Nature Biotechnology*, Volume 14, June 1996) along with numerous other methods which may have slightly lower efficiency rates then those listed. Some of these methods require specific types of cells and other methods can be practiced on any number of cell types.

The use of pollen, cotyledons, meristems and ovum as the target issue can eliminate the need for extensive tissue culture work. However, the present state of the technology does not provide very efficient use of this material.

Generally, cells derived from meristematic tissue are useful. Zygotic embryos can also be used. Additionally, the method of transformation of meristematic cells of cereal is also taught in the PCT application WO96/04392. Any of the various cell lines, tissues, plants and plant parts can and have been transformed by those having knowledge in the art. Methods of preparing callus from various plants are well known in the art and specific methods are detailed in patents and references used by those skilled in the art.

Cultures can be initiated from most of the above identified tissue.

The only true requirement of the transformed material is that it can form a transformed plant. The transgenic gene can come from various non-plant genes (such as; bacteria, yeast, animals, viruses)along with a plant gene.

The DNA used for transformation of these plants clearly may be circular, linear, double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The DNA used for transformation of these plants clearly may be circular, linear, double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The regulatory promoters employed in the present invention can be constitutive such as CaMv35S (usually for dicots) and polyubiquitin for monocots or tissue specific promoters such as CAB promoters, etc. The prior art promoter include but is not limited to octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. Many dicots can easily be transformed with Agrobacterium. Some monocots are more difficult to transform. As previously noted, there are a number of useful transformation processes. The improvements in transformation technology are beginning to eliminate the need to regenerate plants from cells. Since 1986, the transformation of pollen has been published and recently the transformation of plant meristems have been published. The transformation of ovum, pollen, and seedlings meristem greatly reduce the difficulties associated with cell regeneration of different plants or genotypes within a plant can present. Duncan, from at least 1985–1988 produced literature on plant regeneration from callus. Both inbred and hybrid callus have resulted in regenerated plants. Somatic embryogenesis has been performed on various maize tissue which was considered unusable for this purpose. The prior art clearly teaches the regeneration of plants from various maize tissues.

The most common method of transformation is referred to as gunning or microprojectile bombardment. This biolistic process has small gold coated particles coated with DNA shot into the transformable material. Techniques for gunning DNA into cells, tissue, callus, embryos, and the like are well known in the prior art.

After the transformation of the plant material is complete, the next step is identifying the cells or material which has been transformed. In some cases, a screenable marker is employed such as the beta-glucuronidase gene of the uldA locus of *E. coli*. Thus, the cells expressing the colored protein are selected for either regeneration or further use. In many cases, the transformed material is identified by a selectable marker. The putatively transformed material is exposed to a toxic agent at varying concentrations. The cells which are not transformed with the selectable marker that provides resistance to this toxic agent die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. If the transformed material was cell lines then these lines are regenerated into plants. The cell's lines are treated to induce tissue differentiation. Methods of regeneration of cellular maize material are well known in the art since early 1982. The plants from either the transformation process or the regeneration process or crossed to either such plants or a progeny of such plants are transgenic plants.

The invention encompasses the inbred corn line used in crosses with other, different, corn inbreds to produce (F1)

corn hybrid seeds and plants with the characteristics that make good hybrids. This invention includes cells which upon growth and differentiation produce corn plants having the physiological and morphological characteristics of the inbred line ZS01220.

European Patent Application, publication 160,390, describes tissue culture of corn which can be used by those skilled in the art. Corn tissue culture procedures are also described in the literature as early as 1982.

A deposit of at least 2500 seeds of this invention will be maintained by Garst Seed Company, 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material will be removed upon issuance of any granted patent claims of this application by depositing at least 2500 seeds of this invention at the American Type Culture Collection, Rockville, Md. The deposit of at least 2500 seeds will be from the same inbred seed taken from the deposit maintained by Garst Seed Company. The ATCC deposit will be maintained in that depository, which is a public depository, for a period of 30 years, or 5 years after the last request, or for the effective life of the patent, whichever is longer, and will be replaced if it becomes nonviable during that period.

Additional public information on some ZS designations may be available from the PVP office a division of the US government.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Inbred corn seed designated ZS01220, seed of which has been deposited in the ATCC accession number 209964.

2. A corn plant produced by the seed of claim 1.

3. A tissue culture of regenerable cells of ZS01220 of claim 1 wherein the tissue culture regenerates plants capable of expressing the phenotype of ZS01220.

4. A tissue culture according to claim 3, the tissue culture selected from the group consisting of leaves, pollen, embryos, roots, root tips, anthers, silk, flowers, kernels, ears, cobs, husks and stalks, and cells and protoplasts therefrom.

5. A corn plant capable of expressing the phenotype of ZS01220 regenerated from the cells of the tissue culture of claim 3.

6. Hybrid seed produced by:
   (a) planting, in pollinating proximity, seeds of corn inbred lines ZS01220 which has been deposited in the ATCC accession number 209964 and another inbred line, one of said inbred lines not releasing pollen;
   (b) cultivating corn plants resulting from said planting;
   (c) allowing cross pollinating to occur between said inbred lines; and
   (d) harvesting seeds produced on the non pollen releasing inbred.

7. Hybrid seed produced by hybrid combination of plants of inbred corn seed designated ZS01220 of claim 1 and plants of another inbred line.

8. Hybrid plants grown from seed of claim 7.

9. A first generation (F1) hybrid corn plant produced by using ZS01220 which has been deposited in the ATCC accession number 209964 the process of:
   (a) planting, in pollinating proximity, seeds of corn inbred lines ZS01220 deposited in the ATCC accession number 209964 and another inbred line;
   (b) cultivating corn plants resulting from said planting;
   (c) preventing pollen production by the plants of one of the inbred lines;
   (d) allowing natural cross pollinating to occur between said inbred lines;
   (e) harvesting seeds produced on plants of the inbred line of step (c); and
   (f) growing a harvested seed of step (e).

10. A tissue culture of the regenerable cells of the corn plant of claim 8.

11. A tissue culture of the regenerable cells of the corn plant of claim 9.

12. A corn plant, isogenic to the corn plant according to claim 2, said plant comprising at least one transgene, wherein the transgene is selected from the group consisting of *Bacillus thuringiensis* genes expressing insect resistance, Pat gene, Bar gene and EPSP gene expressing herbicide resistance.

13. A seed from the plant according to claim 12 including at least one of said transgenes.

14. Hybrid seed containing at least one of said transgenes, said seed produced by hybrid combination of isogenic plants of inbred corn seed designated ZS01220 in claim 13 and plants of another inbred line.

15. A corn plant, isogenic to the corn plant according to claim 2, said plant comprising at least one mutant gene selected from the group consisting of: sugary 1, shrunken 1, waxy, ea which express as starch mutations, imazethapyr-tolerant genes, $IT_{tm}$ and $IR_{tm}$ which expresses herbicide tolerance.

16. A seed from the plant according to claim 15, including at least one of said mutant genes.

17. Hybrid seed containing at least one said mutant genes said seed produced by hybrid combination of plants of inbred corn seed designated ZS01220 in claim 16 and plants of another inbred line.

18. A corn plant having all of the morphological and phenotypical traits of ZS01220, seed of which has been deposited in the ATCC accession number 209964.

19. A corn plant isogenic to the plant of claim 2, said corn plant comprising at least one transgene.

20. A corn plant isogenic to the plant of claim 2, said corn plant comprising at least one mutant gene.

21. An isogenic corn plant derived from the plant of claim 2 which is isogenic to said plant comprising the addition of a single gene.

22. An isogenic corn plant derived from the seed of claim 1 which is isogenic to said plant comprising the addition of a single gene.

* * * * *